(12) United States Patent
Nygard (10) Patent No.: US 9,753,150 B2
(45) Date of Patent: Sep. 5, 2017

(54) LOW-RATE INEXPENSIVE DIGITAL γ-RAY IMAGING/INSPECTION SYSTEM

(71) Applicant: Sharpxview AS, Asker (NO)

(72) Inventor: Einar Nygard, Asker (NO)

(73) Assignee: Sharpxview AS, Asker (NO)

( * ) Notice: Subject to any disclaimer, the term of this patent is extended or adjusted under 35 U.S.C. 154(b) by 530 days.

(21) Appl. No.: 14/493,982

(22) Filed: Sep. 23, 2014

(65) Prior Publication Data

US 2016/0084967 A1    Mar. 24, 2016

(51) Int. Cl.
| G01N 23/18 | (2006.01) |
| G01T 1/20 | (2006.01) |
| G01T 1/208 | (2006.01) |
| G01N 23/04 | (2006.01) |

(Continued)

(52) U.S. Cl.
CPC ........... *G01T 1/2018* (2013.01); *G01N 23/04* (2013.01); *G01N 23/18* (2013.01); *G01T 1/202* (2013.01); *G01T 1/208* (2013.01); *G01T 7/00* (2013.01); *G01N 2223/202* (2013.01);

(Continued)

(58) Field of Classification Search
CPC .... G01N 23/04; G01N 23/046; G01N 23/083; G01N 23/087; G01N 23/10; G01N 23/18; G01N 2223/202; G01N 2223/205; G01N 2223/33; G01N 2223/3303; G01N 2223/628; G01N 2223/629; G01N 2223/646; G01N 2223/6462

See application file for complete search history.

(56) References Cited

U.S. PATENT DOCUMENTS

| 4,278,886 A | | 7/1981 | Wallace | |
| 4,365,339 A | * | 12/1982 | Pavkovich | ............. A61B 6/032 |
| | | | | 378/15 |

(Continued)

FOREIGN PATENT DOCUMENTS

| CA | 2161347 | 11/1994 |

OTHER PUBLICATIONS

Sharpxview-1, Low-Rate Inexpensive Digital Gamma-Ray Imaging/Inspection System, PCT Serial No. PCT/IL2015/050945, filed Sep. 18, 2015, International Search Report, dated Jan. 25, 2016.

(Continued)

*Primary Examiner* — Thomas R Artman
(74) *Attorney, Agent, or Firm* — Schmeiser, Olsen & Watts LLP (57) ABSTRACT

A γ-ray scanner includes a Solid-State Single-Photon Detector ("SSSPD") and a γ-ray source, which may be a radioisotope such as Americium oxide (Am-241) that may not require certification since it has a low intensity that is safe even over extended periods of exposure to a human body. The γ-ray scanner may be used for monitoring a fixed object such as a pipe and includes an imaging assembly having a stationary annular gantry surrounding the pipe and an armature that fixedly supports the γ-source and the detector in mutual opposed alignment, so that they are constrained to move together. The armature rides around an inside periphery of the gantry, while the armature or the gantry moves laterally in a direction parallel to a rotation axis of the armature so as to move the γ-ray beam around and along the pipe.

18 Claims, 9 Drawing Sheets

(51) Int. Cl.
*G01T 1/202* (2006.01)
*G01T 7/00* (2006.01)
(52) U.S. Cl.
CPC .............. *G01N 2223/301* (2013.01); *G01N 2223/3303* (2013.01); *G01N 2223/628* (2013.01); *G01N 2223/646* (2013.01)

(56) References Cited

U.S. PATENT DOCUMENTS

| | | | | |
|---|---|---|---|---|
| 4,671,102 A * | 6/1987 | Vinegar | ............... | G01N 15/042 250/573 |
| 5,042,055 A * | 8/1991 | Wirt | ............... | G01N 23/18 378/56 |
| 5,090,039 A * | 2/1992 | Gard | ............... | E21B 17/006 250/268 |
| 5,698,854 A * | 12/1997 | Gupta | ............... | G01N 23/18 250/358.1 |
| 7,656,997 B1 * | 2/2010 | Anjelly | ............... | G01N 23/04 378/59 |
| 7,885,381 B2 * | 2/2011 | Nagumo | ............... | G01B 15/025 378/41 |
| 8,119,980 B2 * | 2/2012 | Malmin | ............... | G01T 1/1648 250/252.1 |
| 8,759,780 B2 * | 6/2014 | Dobbs | ............... | G01B 15/02 250/360.1 |
| 9,217,720 B2 * | 12/2015 | Prentice | ............... | B23K 31/125 |
| 9,244,024 B1 * | 1/2016 | Patterson | ............... | G01N 23/18 |
| 2008/0083870 A1 * | 4/2008 | Malmin | ............... | G01T 1/40 250/252.1 |
| 2008/0267345 A1 * | 10/2008 | Nagumo | ............... | G01B 15/025 378/11 |
| 2011/0095172 A1 * | 4/2011 | Malmin | ............... | G01T 1/1648 250/252.1 |
| 2011/0168900 A1 * | 7/2011 | Dobbs | ............... | G01B 15/02 250/360.1 |
| 2012/0201347 A1 * | 8/2012 | Prentice | ............... | B23K 31/125 378/59 |
| 2016/0033425 A1 * | 2/2016 | Patterson | ............... | G01N 23/18 378/60 |
| 2016/0084967 A1 * | 3/2016 | Nygard | ............... | G01T 1/2018 378/59 |
| 2016/0266055 A1 * | 9/2016 | Phin | ............... | G01N 23/18 |
| 2016/0313263 A1 * | 10/2016 | Featonby | ............... | G01N 23/18 |
| 2016/0370303 A1 * | 12/2016 | Schmitz | ............... | G01N 23/083 |
| 2017/0030844 A1 * | 2/2017 | Campbell | ............... | G01N 23/18 |
| 2017/0082556 A1 * | 3/2017 | Bueno | ............... | G01N 23/04 |

OTHER PUBLICATIONS

Konstantinos Spartiotis, et al., X-and Gamma Ray Imaging Systems based on CdTe-CMOS Detector Technology, 2008 IEEE Nuclear Science Symposium Conference Record, dated Nov. 14, 2008, pp. 518-522, Finland.

Konstantinos Spartiotis, et al., A photon counting CdTe gamma- and X-ray camera, Nuclear Instruments and Methods in Physics Research, Section A 550 (2005) 267-277, dated Feb. 18, 2005, pp. 266-277, Finland.

Bam, TomoCAR for X-Ray-Planar-Tomography, dated May 2014, pp. 1-3.

U. Ewert, et al., Mobile Computed Tomography for Inspection of Welded Pipes, pp. 1-6, Germany.

B. Redmer, et al., TomoCAR—Tomographical Computer-Aided Radiology—a New Testing Method for the Visualisation and Sizing of Defects in Circumferential Seams, 6th International Conference on NDE in Relation to Structural Integrity for Nuclear Pressurized Components, Budapest, Hungary, dated Oct. 2007, pp. 1-11.

Van Der Ent, Jan, Digital Radiographic Inspection replacing traditional RT and 3D RT Development, dated Mar. 2014, pp. 1-26, Geneva.

* cited by examiner

LOW-RATE INEXPENSIVE DIGITAL γ-RAY IMAGING/INSPECTION SYSTEM

FIELD OF THE INVENTION

This invention relates to low-rate digital γ-ray imaging and inspection.

BACKGROUND OF THE INVENTION

Most X-ray inspection/imaging systems sold on the market are complex, versatile and expensive systems (US$10,000, for instance, would not buy very much, if anything at all). Typical systems also come equipped with a high-intensity X-ray generator that is instantaneously hazardous if exposed to humans. Consequently, current X-ray systems are well beyond the purview of the ordinary consumer, both because of the high price and because of the danger.

Lower X-ray intensity compares with less light if seen in analogy with ordinary photography and a very low X-ray intensity could therefore be compared with taking a photo in near darkness. In both photography and X-ray imaging this leads to a longer exposure time. For the most traditional digital X-ray detectors, very long exposure has been a problem that is caused by the inherent properties of those detectors (i.e. integrating-mode type detectors with too high dark-currents for long integrations). A different technique exists however, using detectors formed of solid-state sensor material that are responsive to single photons (named here "Solid-State Single-Photon Detectors" (SSSPD)). Such technology is not new, but has still encountered stiff competition from the integrating-mode type detectors for mainstream usage despite having several advantageous properties.

It would desirable and would offer many commercial advantages to provide a portable, low-rate digital imaging/inspection system based on the use of SSSPD and employing a γ-ray source of such low rate that certification is unnecessary.

SUMMARY OF THE INVENTION

An object of the invention is to provide a portable, low-rate digital γ-ray imaging/inspection. In different implementations, such a system has the following features:
Light weight
Battery operation possibility (i.e. low power)
(wireless) operation through portable computer (e.g. mobile phone)
Better accessibility for all users by virtue of:
  Low cost
  Uses a very low rate γ-ray source that preferably requires no certification
  Easy operation/training While the system may be portable, the invention does not preclude also permanent installations.

One particularly winning property of the SSSPD is its ability to handle ultra-low γ-ray rates. This property of the SSSPD is a feature that is not yet commercially explored and is a key element of the present invention.

Another key element of the present invention is to combine the above mentioned SSSPD ultra-low rate quality with a γ-ray generating device that produces γ-rays at a rate that is very low in comparison to conventional X-ray generators. This may be achieved by the use of a radioisotope source rather than an X-ray generator. One particular radioisotope source that may be used is of the kind employed in conventional smoke alarms whose rate is so low that it is commercially available "off-the-shelf" as a part of the smoke alarm without the need for any certification, training or other security measures.

Such a smoke alarm radioisotope source consists of approximately 0.2 mg of the material Americium oxide (Am-241) with an α-activity of ~35 kBq. It is primarily an α-emitting source but the α rays can easily be blocked and the (by-product) γ rays can be used as the "X-ray generator" equivalent. We refer here to such source as a "γ-source", although for our purposes the term "γ-ray" or "γ-source" is interchangeable with "X-ray" as this is the common term used for imaging. It will be appreciated that γ-rays and X-rays are both photons and are indistinguishable if at same wavelength: their only difference being how they originate.

Naturally, the benefit of the concept described above is achieved at the expense of the speed of the imaging/inspection, which will be very slow compared with conventional systems. On the other hand, it will be:
Possible to produce at very low cost
Possible to render suitable for use without X-ray certification, protection etc.

There are numerous applications where the speed of the imaging/inspection is of lesser importance than these benefits.

Using a radioisotope as the "X-ray machine" is known per se. The significance of the present invention is that provided its energy falls within a range that permits detection by the sensor, any γ-ray radioisotope can be used and that it is typically chosen based on its wavelength- (energy-) characteristics combined with the type of material to be inspected for achievement of optimal contrast. The higher the rate, or Becquerel- (Bq-) value of the source, the faster the imaging, and if speed is the top priority, a source with too high a Bq-value will be hard to find although it will of course require certification and will therefore not be available for common household use as an "off-the-shelf" item.

On the other hand, the above-mentioned smoke alarm radioisotope, Am-241, which has an α-activity of ~35 kBq and usable γ energies of 13.9 keV and 59.5 keV (with activity similar to the α-activity), has the special and very useful property of being "certified" for common household use and thereby for everyone to handle. A particularly advantageous embodiment of the invention exploits this property and therefore the invention will be described with particular regard to this source.

Features and Applications

Typically, the features of the system according to the invention will address the following needs:
  where cost is a dominant factor i.e. in many cases since conventional systems are typically out of reach not only for most private household budgets but also for many small workshops and work-departments;
  where ease-of-use is a dominant factor, since the invention avoids the usually cumbersome process of certification/regulatory-permission to use conventional high-radiation systems, and also avoids costs relating to training and possible customization;
  where portability is a dominant factor, as the system according to the invention is very light compared with conventional systems and also can operate on batteries; and
  where there is a need for a permanently installed system for inspection of for instance a stationary object over long time. One example might be looking for occurrence of corrosion or leaks e.g. in a water-pipe, and even more if there is a need for a multitude of such permanently installed systems.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 9 to 12d show pictorially different applications of the system according to the invention.

DETAILED DESCRIPTION OF EMBODIMENTS

In the following description of some embodiments, identical components that appear in more than one figure or that share similar functionality will be referenced by identical reference symbols.

Figure 1:
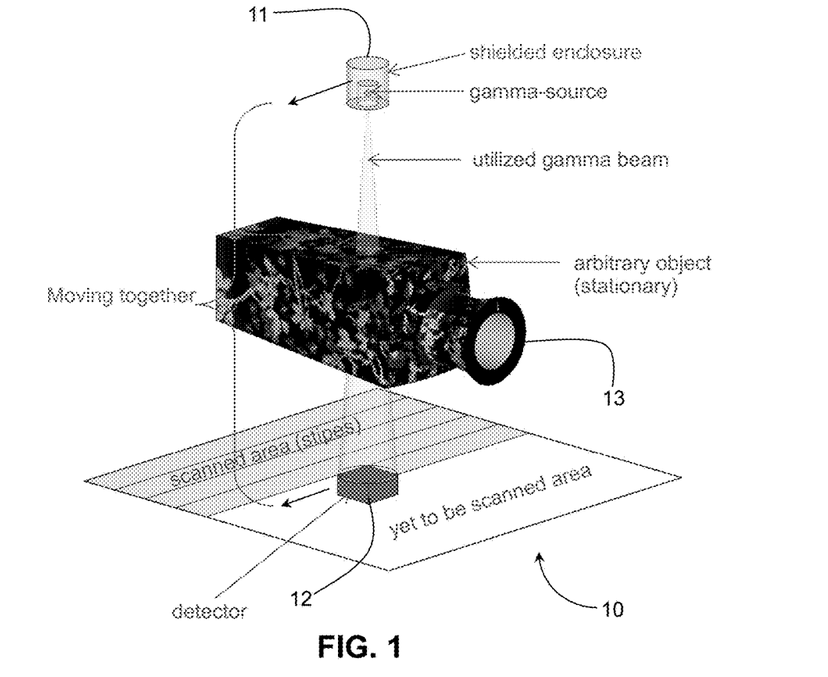
FIG. 1 is a pictorial representation of a low-cost, low rate γ-ray scanner having a low-rate γ-source according to an embodiment of the invention.

FIG. 1 is a pictorial representation of a low-cost, low rate γ-ray scanner 10 comprising a low-rate γ-source 11 and a Solid-State Single-Photon Detector (SSSPD) 12. Arranging a γ-source 11 and an SSSPD 12 as depicted in FIG. 1, and scanning both of them together across (or around) an object 13, permits use of a small area SSSPD. This also creates the potential for a very low cost γ-ray inspection system, since this kind of γ-source is very inexpensive (range ~US$1).

Figure 2:
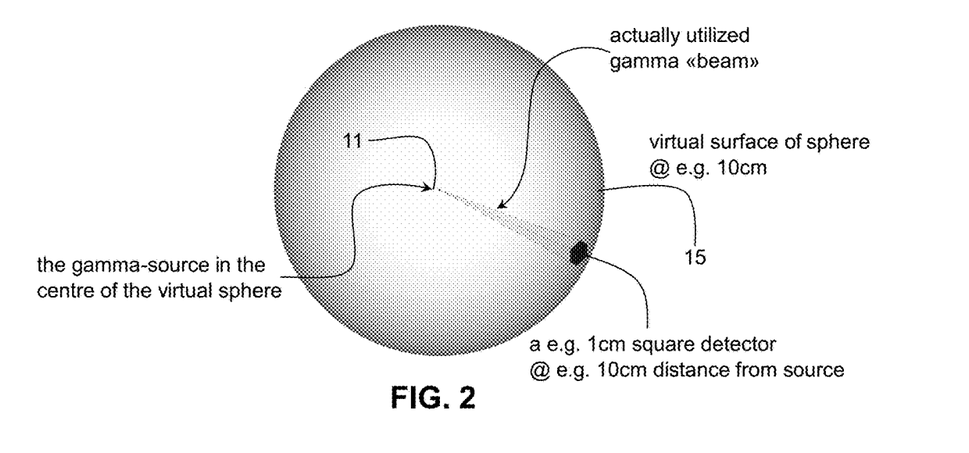
FIG. 2 shows schematically a suitable γ-source as a point-source at the centre of a virtual sphere.

FIG. 2 shows schematically the γ-source 11 as a tiny, i.e. point-source at the centre of a virtual sphere 15. Unless screened in some directions, the source will radiate in all directions and at any given spherical distance the γ rate will be equal at every point on the spherical surface.

The surface (A) of the virtual sphere is:

$$A = 4\pi r^2 \quad (1)$$

where r=radius of sphere=distance from source

The γ rate, N, arriving per given defined area of the surface, a, is:

$$N = \frac{a}{A} \cdot N_0 = \frac{a}{4\pi r^2} \cdot N_0 \quad (2)$$

where $N_0$=γ emission rate of the source.

For a smoke detector source, $N_0$ is the emission rate of the γ rays which is almost the same as the specified α-activity (35 kBq) meaning that it emits about 35,000 γ-photons per second.

Assuming further that we place a detector with one square-cm surface (a) 10 cm away from the source (r) (depicted also in FIG. 2), and the open air γ rate on the surface of this detector will be:

$$\frac{1(\text{cm}^2)}{4\pi \cdot 100(\text{cm}^2)} \cdot 35,000 = 27.9 \quad (3)$$

i.e., approximately 28 γ-rays per second will hit the surface of the detector when there are no obstacles between the source and the detector.

The Detector

A major aspect of the present invention is that such very low rate of rays (X-rays or γ-rays), actually can be utilised for real usage γ-ray imaging/inspection, albeit not with a conventional digital detector (i.e. the integrating-mode type detectors), but with an SSSPD. Obviously, it is a slow process but the image can be of high quality in cases where the object for the imaging/inspection is stationary for the entire (long) duration it will take.

Figure 3:
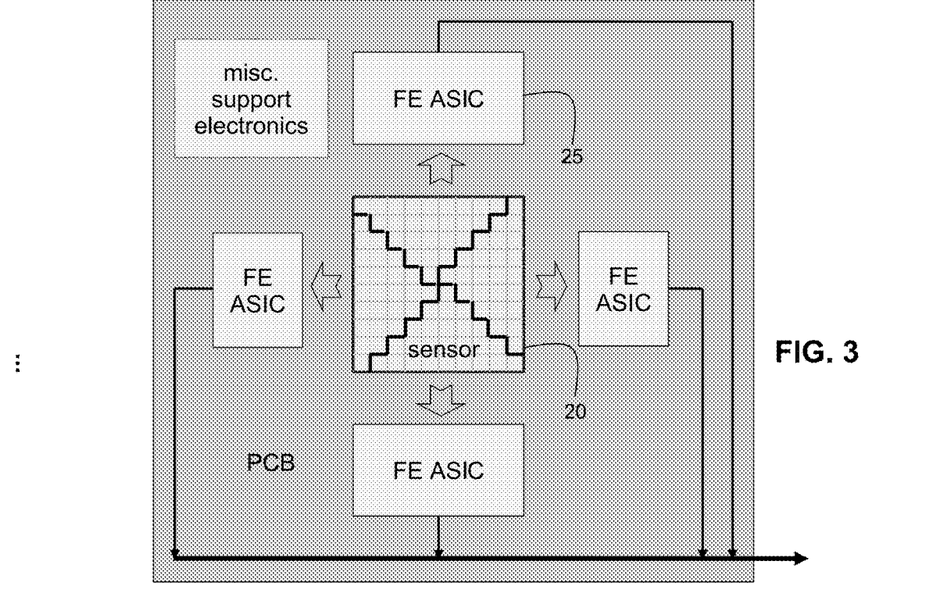
FIG. 3 is a block diagram showing the principal functionality of a detector for use with the system of FIG. 1.

FIG. 3 is a block diagram showing the principal functionality of the detector 12 according to an embodiment of the invention, comprising a sensor 20 formed of a single monolithic crystal of Cadmium-Zinc-Telluride (CZT) or Cadmium-Telluride (CdTe), and sub-divided (pixelated) in a 2D matrix of pixels 21. The size of each pixel is about 1 mm by 1 mm, the number of pixels being typically 10×10, in which case the entire sensor (-crystal) surface is about 10 mm×10 mm. The thickness of the sensor (-crystal) is about 1 mm. Each pixel of the sensor is attached to a respective active readout circuit 22 (shown in FIG. 4), which is separate to the crystal but is coupled thereto by a respective connecting signal line.

The individual readout circuits 22 thus total the same number as the total number of pixels and each circuit belongs to, i.e. is connected to, a corresponding unique pixel in the sensor 20. In such an arrangement there is consequently a total of 100 readout circuits each constituting a discrete electronics channel. A selected number of channels or pixels are grouped into an Application Specific Integrated Circuit (ASIC) 25, a working example of which is shown schematically in FIG. 4.

Figure 4:
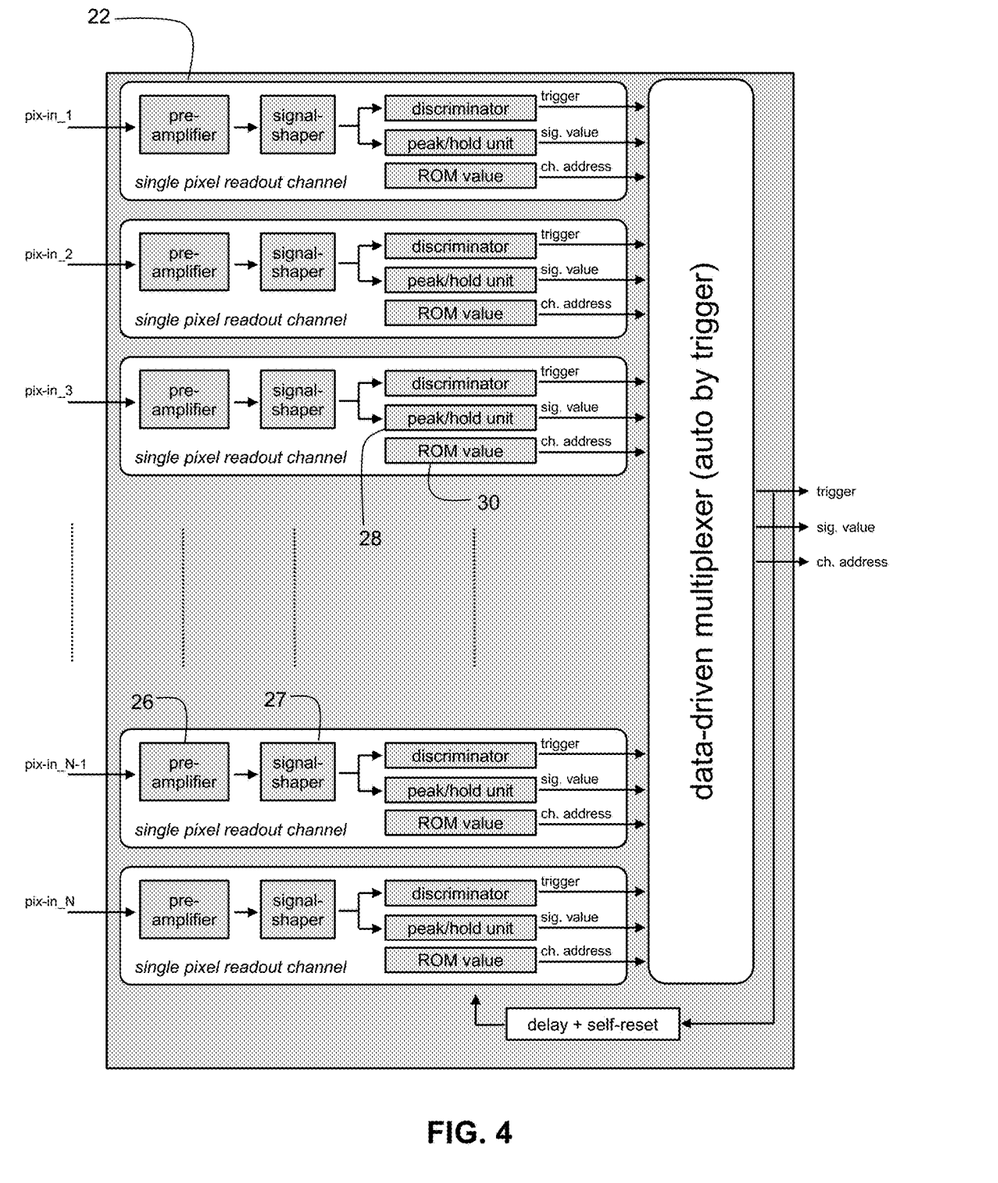
FIG. 4 shows schematically a detail of an Application Specific Integrated Circuit (ASIC) for use with the detector of FIG. 3.

Here, assuming the sensor has 100 pixels, 25 channels are bundled into one (Front-End (FE-) ASIC), and four identical such ASICs are placed one on each side of the sensor and handle 25 pixels each. Typically the 25 pixels form a triangle whose base is an edge and whose apex is the centre of the crystal (these four triangles are illustrated in the drawing with thick lines).

Figure 5:
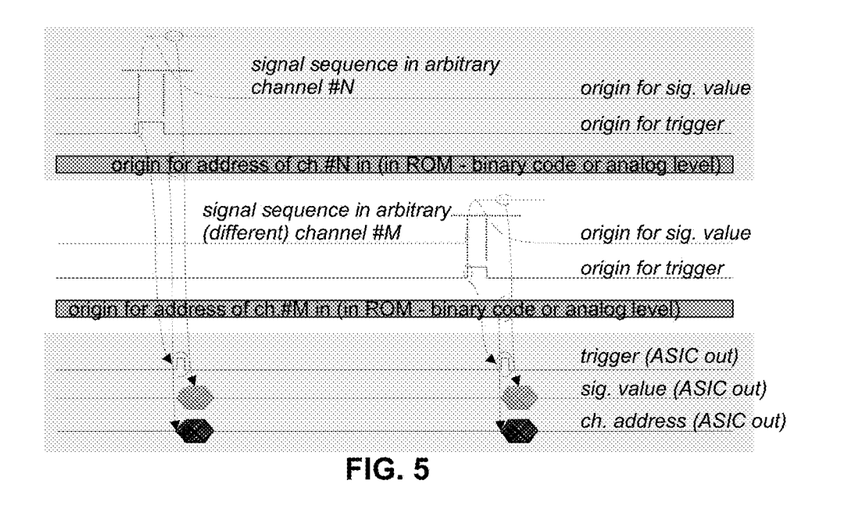
FIG. 5 is a timing diagram relating to operation of the ASIC shown in FIG. 4.
Figure 6:
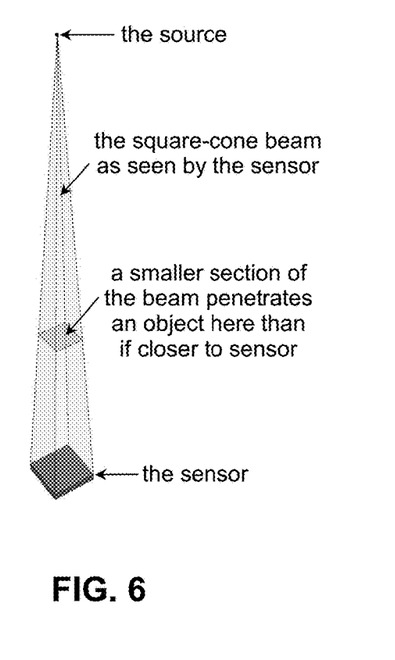
FIG. 6 shows the active area coverage of the gamma beam as function of the longitudinal position between the source and the object.

FIGS. 5 and 6 depict an electronic implementation that is well-suited for the low γ- (X-ray) rates employed.

When a photon (γ-ray/X-ray) strikes a pixel in the sensor, an electronic charge is released that is proportional to the energy of the photon. Each pixel readout circuit 22 comprises a pre-amplifier 26 and a signal-shaper 27 (FIG. 4) that respectively amplifies and shapes the signal into a semi-Gaussian looking pulse in FIG. 5 (labelled "origin for sig. value"). Further electronics inside each readout circuit 22 include a peak-hold/stretcher device 28, a discriminator 29 and a ROM cell 30 which operate, in a data-driven manner, to push out the peak-value of the signal, a digital trigger, and a unique in address for the actual pixel. This unique address can be in the form of an analog level, or as a conventional binary code. The readout circuit 22 may be constructed similar to that described in U.S. Pat. No. 6,153,882 in the name of the present inventor and whose contents are fully incorporated herein by reference.

These three signals are auto-multiplexed through a data-driven multiplexer 31 that serves all 25 channels in the FE-ASIC 25 so that they appear on three respective common outputs of the ASIC. This occurs with substantially no data-loss caused by coincident events, due to the low rate. In FIG. 5 there is depicted another channel (#M) which also receives and processes an event, in parallel but at a later time. At the bottom of this figure is depicted the output of both events, pushed out from the ASIC on the same data-lines.

Resolution Versus Image Capture Speed

The sensor shown by way of example in FIG. 3 has 10×10 pixels covering 1 mm square each, so that in total it covers 1 cm² and has 100 pixels in total ($P_{no}$=100). Consider the case that an 8-bit image grey scale resolution will suffice for these low-end products and that the desired average number of counts per pixel (cpp) is 200 if performing an open air image (i.e. without any intervening object obstructing the view between the source object and the sensor). With the rate exemplified in expression 3 (i.e. N=28 γ photons per second), the total image capture time ($T_{cap}$) would then be:

$$T_{cap} = \frac{cpp}{N} \cdot P_{no} = \frac{200}{28} \cdot 100 = 714 \text{(seconds)} \quad (4)$$

i.e. almost 12 minutes. This is just for generating an image in one detector position. In order to image a larger object as would usually be required, the value of $T_{cap}$ would need to be multiplied by the number of steps needed to scan the larger area. Also, as seen by the sensor, the γ-photons are emitted within a conical "beam" having a square cross-section as shown in FIG. 6 that originates from the source. Therefore, the scanned area of any part of the object whose distance from the source is less than that of the detector (i.e. any feature that is intermediate the source and the detector) will be less than the 1 cm² coverage of the sensor. As a result, any such features will be overlooked during a single step of the sensor and it is necessary to stepwise move the sensor by smaller steps than 1 cm at a time to fully cover the object.

Thus, in order to step-scan e.g. 10 cm×10 cm, it might be necessary to make 400 steps or more, and for each step, the $T_{cap}$ is required, and the full image would take 80 hours (~3 days). There are three ways to reduce this imaging time (easily deduced from expression 4):

1. Increasing the activity of the source (i.e. increasing N)
2. Reducing the contrast (by reducing the requirement of cpp)
3. Reducing the number of pixels ($P_{no}$)

Option 1 would cause regulatory problems if only the smoke detector source requires no regulation and is therefore not always an option, although doable of course. Option 2 will just reduce the contrast quality and is therefore an option that depends on the user's requirement and is automatically achieved by increasing the stepping speed. Option 3 is achievable without replacing the sensor by combining (summing) the pixels to form larger ones using software/firmware.

Figure 7:
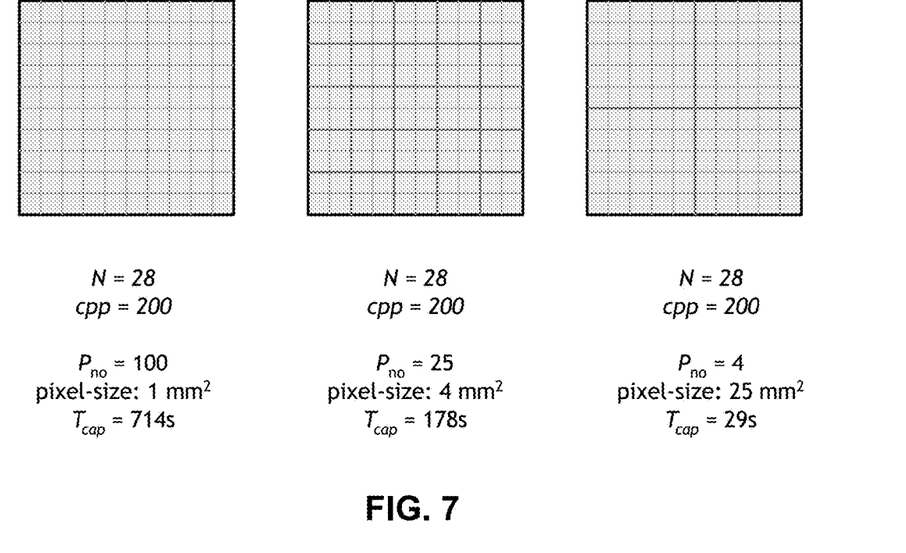
FIG. 7 shows schematically how pixel binning may be used to vary the scan time of the system.

Using Option 3 would obviously reduce the spatial resolution if exactly the same geometry relating to the relative positions between the source, the object and the sensor were preserved. However, in practice the imaging system may be designed to compensate for potential reduction in spatial resolution by locating the object closer to the source where the effective intensity is more concentrated owing to the conical shape of the γ-beam. This can actually increase the effective resolution of the detector owing to the reduction of the covered area of the object in proportion to the object's position between the source and the sensor. This makes reduction of the sensor resolution a sensible thing to do in many cases. In a 10×10 pixel configuration, the binning of pixels can be done logically (i.e. raw-data binning) as shown in FIG. 7 whereas through software they might be binned at any resolution. As can be seen in this example, binning the sensor into just 4 (binned-) pixels, the capture speed increases by 25 times. If this is combined by a reduction of the required cpp to e.g. 100, the overall speed would increase by 50 times, and the 80 hour (~3 day) total imaging duration in the example above would be reduced to just about 1.5 hours.

Thus, depending on the needs, this γ-ray imaging/inspection system can have imaging capture speeds ranging from extremely slow to tolerably slow.

Auxiliary Electronics (Read-Out and Control)

The above described detector architecture was chosen for providing high performance at low speed, but it also offers the potential for a low-power, low-cost system. These two qualities are important factors overall to this invention, and these also need to be reflected in the read-out and control of the system electronics, which also need to facilitate two other main features, i.e. lightweight and wireless operation. Thus, the read-out and control needs to ensure low-cost, low-power, lightweight and possible wireless functionality.

Figure 8:
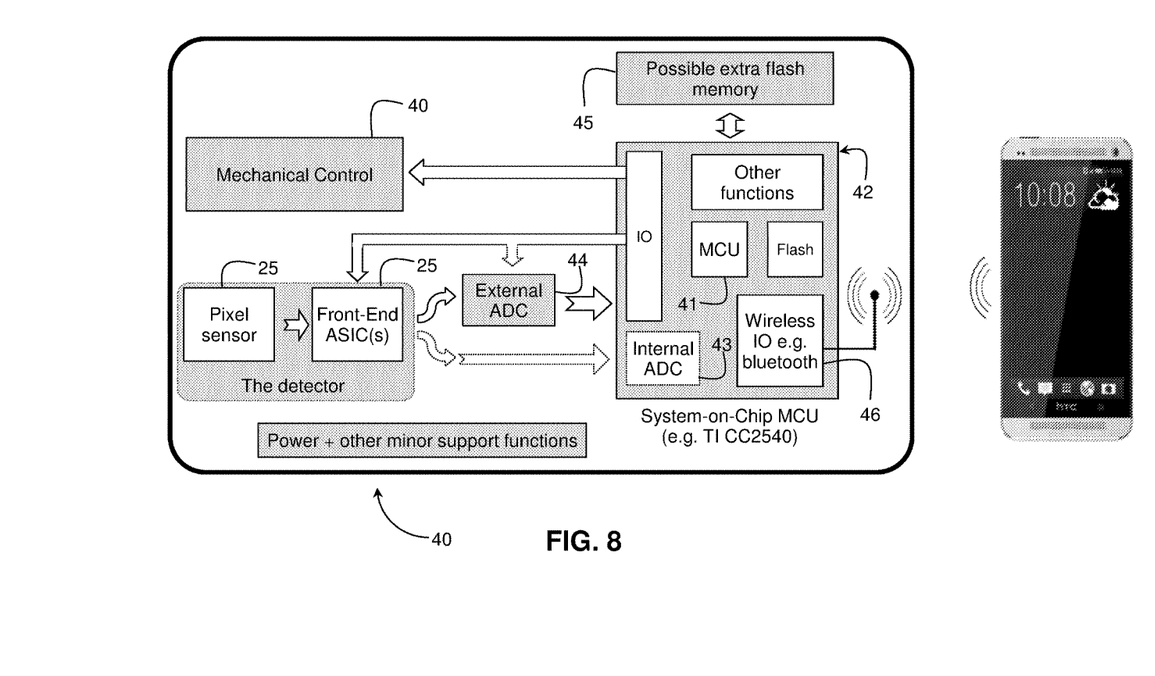
FIG. 8 shows schematically auxiliary detector electronics for read-out and control.

FIG. 8 shows a system 40 that meets these requirements and comprises a micro-controller unit (MCU) 41 constituted by a "System-on-Chip MCU" IC chip ("SoC IC") 42. Several suitable such ICs exist off-the-shelf (produced by e.g. Texas Instruments or Nordic Semiconductor). They are typically inexpensive (a few US$) and the customized FE-ASIC 25 of the detector as described with reference to FIG. 4 can be developed to directly operate hand-in-hand with the SoC IC. Respective Analog-to-Digital Converter(s), ADC(s) 43 are needed to convert the pixel value and possibly the pixel address signals from the FE-ASIC(s). Several ADC-inputs are typically required, and this can be accomplished by using several ADCs, or a single ADC with sufficient parallel input channels. As depicted in FIG. 8, the ADC(s) could be realized by pre-existing components in the SoC IC or by external components shown as 44. Timing/control of the FE-ASIC(s) and the ADCs is handled by the SoC IC.

The SoC IC 42 is also used to control the mechanical scanning movement of the γ-source 11 and the detector 12, and it may interface to possible expansion RAM memory (not shown) if more is needed than available in the SoC IC itself. Likewise, the permanent storage capacity can be extended by auxiliary Flash memory 45.

Optionally, the SoC IC 42 may also have integrated wireless communication capability 46, which may be used to enhance the portability feature of the invention, in combination with e.g. Android/Iphone App software to operate the system. This does not preclude the possibility to use a wired communication e.g. to a desktop computer.

Figure 9:
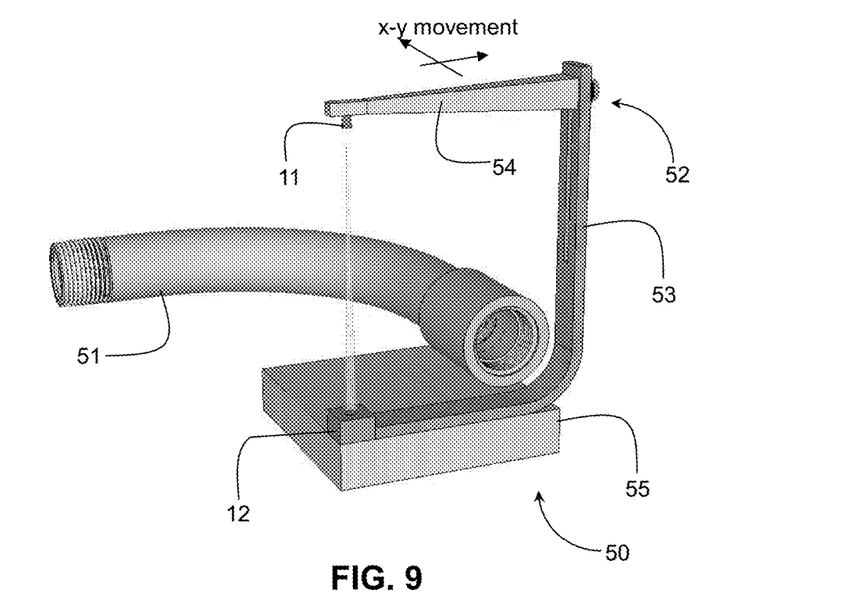
Figure 10:
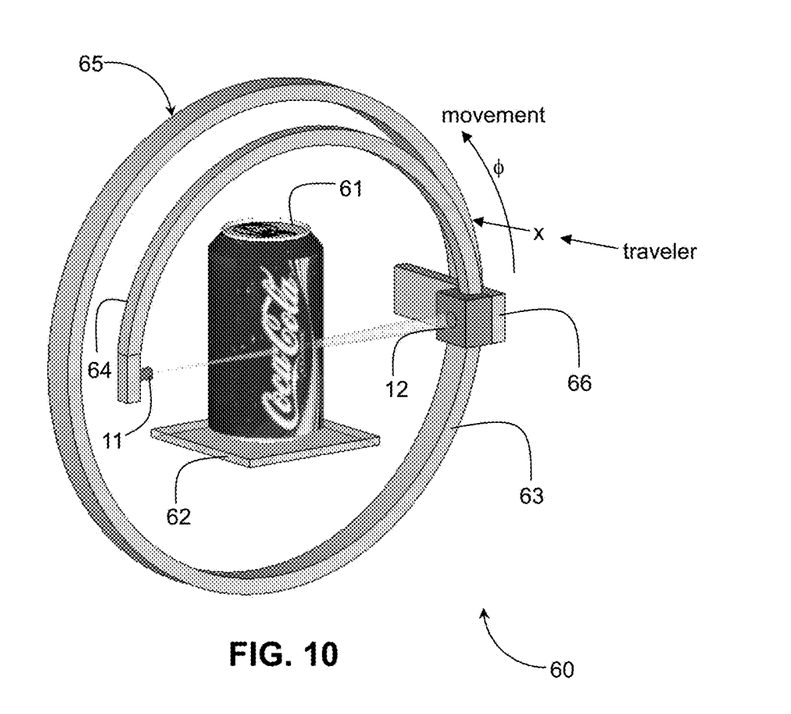
Figure 11:
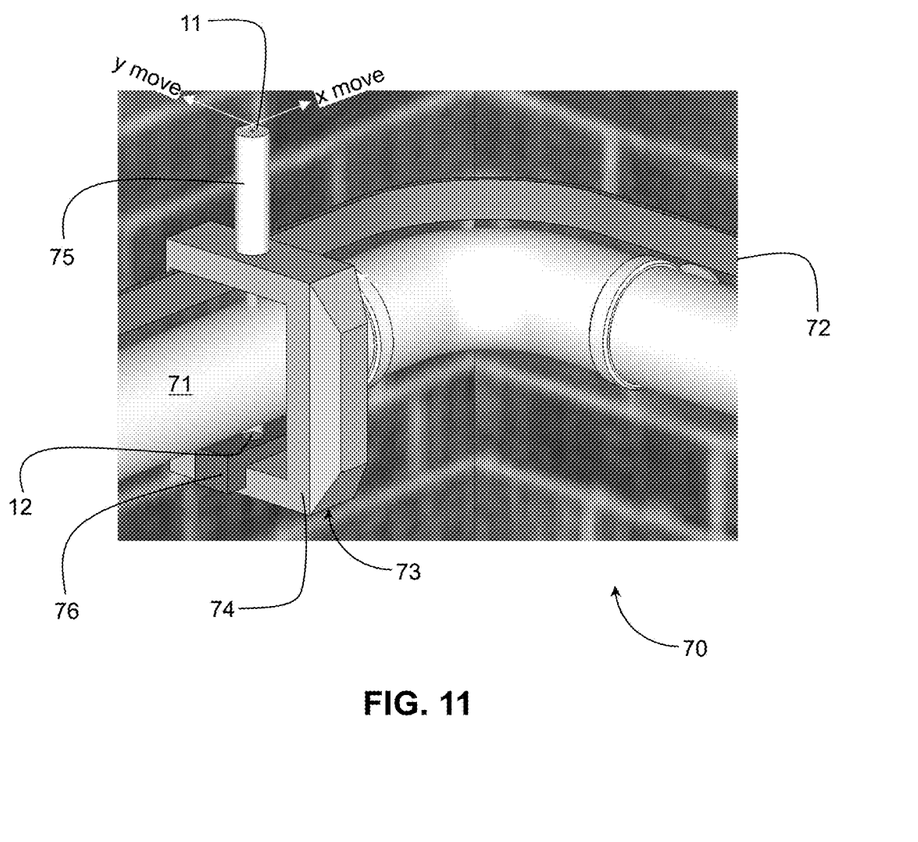

FIGS. 9 to 11 show pictorially different applications of the system according to the invention.

FIG. 9 is an example of a very simple gamma-imager 50 for general purpose 2D imaging use, which employs the same basic concept as depicted in FIG. 1. An object shown by way of example as a pipe 51 is adapted to be γ-ray imaged. The γ-source 11 and the detector 12 are fixed in mutual opposed alignment via an integrated imaging assembly 52 comprising a first arm 53 and a second arm 54. The imaging assembly 52 is connected to the moving element of an x-y table 55. The x-y table 55 moves the imaging assembly 52 in predetermined steps in the x and y directions that are appropriately sized to acquire for each step a γ-ray image fragment of a size (x-y) that is determined by the cross-section of the utilized γ-beam intersecting the object (as described related to FIG. 6). The x-y steps are small enough to make the γ-beam (and the step image-fragments) cover the entire area of the x-y table 55 (typically minus some edge areas). The pipe 51 being imaged must be stationary during this step-scan. All of the step image-fragments are joined together into a full 2D gamma-ray image of approximately the same size as the x-y table 55.

FIG. 10 shows a similar but slightly more advanced system 60 for imaging an object 61 disposed on a fixed platform 62. The system comprises a stationary hollow cylindrical gantry 63 and an arcuate armature 64 that fixedly supports the γ-source 11 and the detector 12 in mutual opposed alignment, so that they are constrained to move together as a unitary imaging assembly 65. The imaging assembly is fixed to a traveler 66 that is configured to ride around the gantry 63 so as to rotate in the φ-direction about a rotation axis x while the imaging assembly 65 is adapted to move linearly back and forth on the traveler 66 parallel to the rotation axis x. Consequently, the γ-ray beam will step circularly (approximately) around center of a circle, as defined by the gantry 63, and back and forth in the x-direction. γ-ray image fragments are thereby acquired at each step, from which both 2D and 3D images of the volume that the beam covers can be reconstructed. The object 61 depicted to be γ-ray imaged is shown by way of example as a can of Coca Cola, which is a registered trademark of the Coca-Cola Company of Atlanta, Ga., USA.

The armature 64 is shown in the figure as arcuate, its radius being sufficiently less than that of the gantry 63 that it is able to rotate completely within the inside periphery of the gantry 63, while being sufficiently large to sweep around the object 61 without obstruction. It will be understood that the shape and dimension of the armature may be varied so long as these requirements are met.

While the system 50 shown in FIG. 9 is comparable to conventional 2D X-ray imaging, the system 60 in FIG. 10 is comparable to CT scan imaging and can therefore also be used for 3D image reconstruction. It is in fact very similar to an ordinary CT, which performs stepped image fragments, the main difference being the physical size of the gantry, the γ-source replacing an X-ray generator, and therefore also the size of the γ-beam. The principle is otherwise the same as for a clinical CT machine.

FIG. 11 shows an example of a more specialized purpose oriented 2D γ-ray inspection system 70 for imaging a pipe 71 in a region of a bend or joint in the pipe, which may be particularly vulnerable to leaks. To this end, an arcuate wall-mounted rail 72 is fixed in close proximity to the pipe 71 so as to follow its shape around the bend. An imaging assembly 73 in the form of a C-shaped gantry 74 supports the γ-source 11 and the detector 12 in mutual opposed alignment, and is moveably supported on the arcuate rail 72 so as to ride along the rail whereby the pipe is stepwise imaged along its length, depicted by the x-axis. The γ-source 11 is attached to the gantry 74 via an extension tube 75 in order to extend the coverage of the conical beam so that γ-photons will image a larger area of the pipe during each imaging step. Movement of the gantry 74 along the rail 72 may be achieved by means of a motor (not shown) attached to the gantry 74 that rotates a wheel having a rubber rim or tire that is in frictional contact with the wall. Rotation of the wheel thus causes it to ride along the wall and induces counter-movement of the gantry along the rail. Alternatively, the rail can have a toothed track that engages a gear wheel that is rotated by a motor mounted on the gantry. In addition to movement of the gantry 74 along the rail 72, the γ-source 11 and the detector 12 are both fixedly attached to a traveler 76 that allows them both to move in tandem laterally along the y-axis as shown in the figure. It will be appreciated that the figure is schematic and details of the attachment of the γ-source 11 to the traveler 76 are not shown, it being understood that the manner of attachment is not a feature of the invention, so long as the γ-source 11 and the detector 12 can move together laterally in mutual alignment. One way to do this is to use a split traveler having tied component travelers at the top and bottom of the gantry with the γ-source 11 and the detector 12 each fixed to a respective one of the component travelers.

Figure 12A:
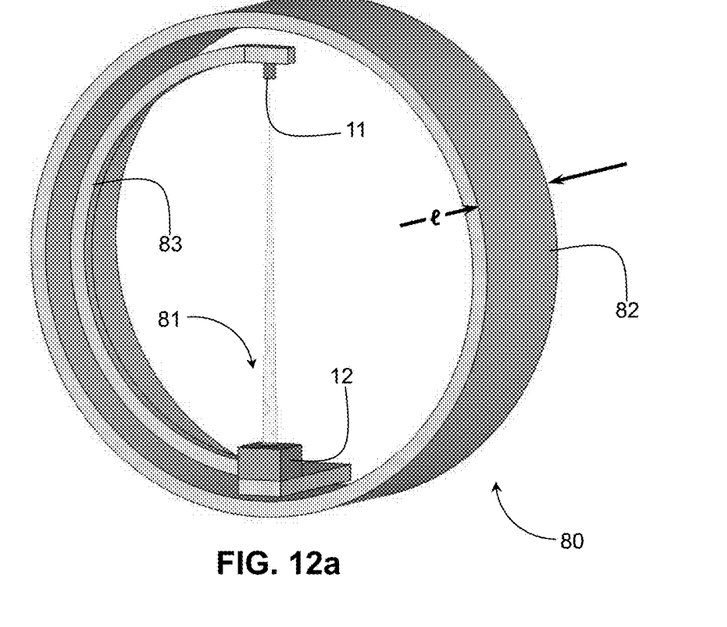
Figure 12B:
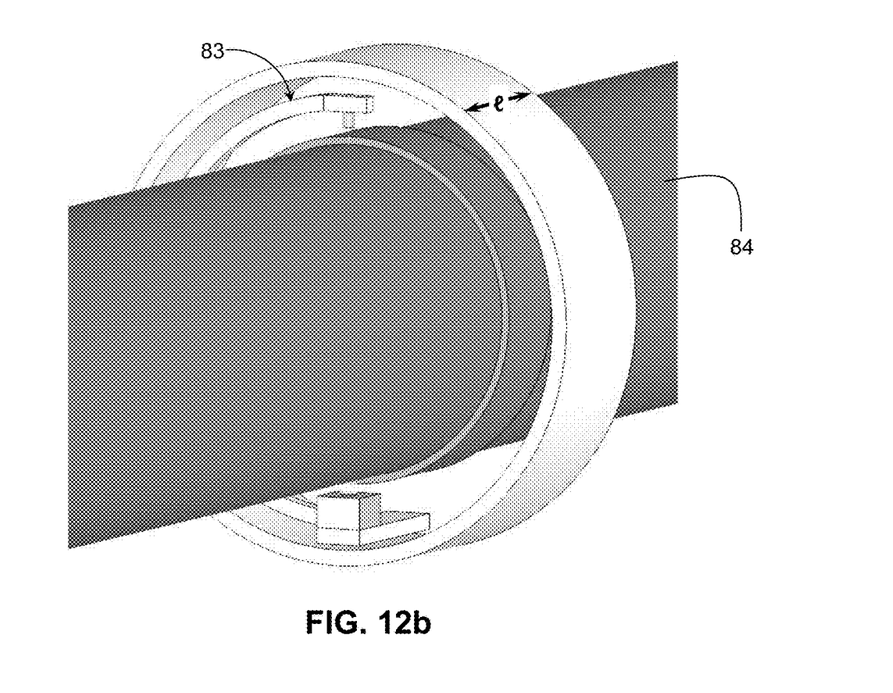
Figure 12C:
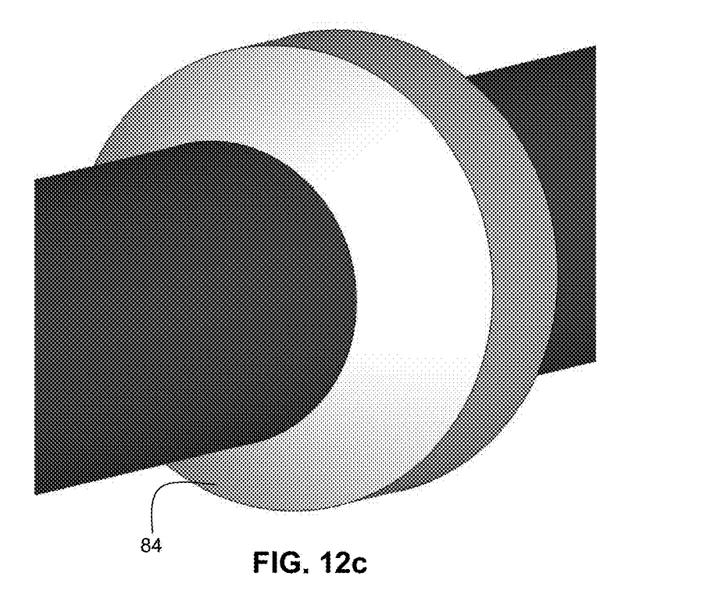
Figure 12D:
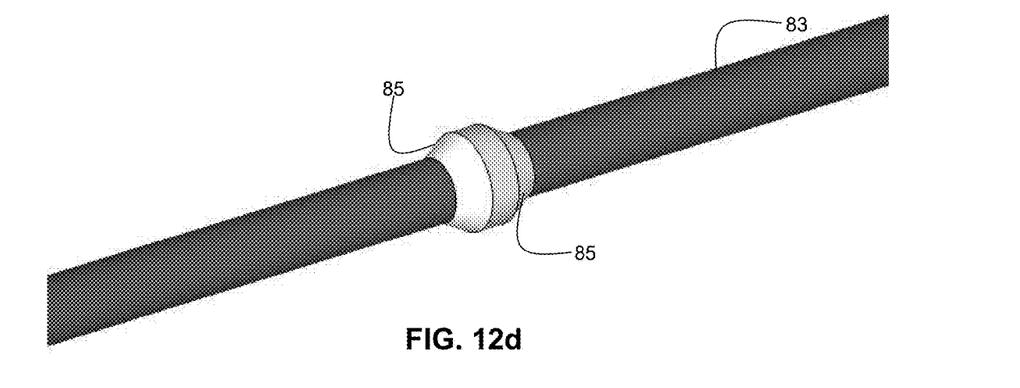

FIGS. 12*a* to 12*d* show an example of a different type of γ-ray imaging system 80 for pipe-inspection. The system 80 is based on a γ-ray imaging assembly 81 depicted in FIG. 12*a* in the form of a cylindrical hollow gantry 82 around whose inside periphery an arcuate armature 83 is configured to rotate in a manner that is identical in principle to the system 60 shown in FIG. 10. The gantry 82 is fixedly mounted around a section of a pipe 84 carrying liquid or gas as depicted in FIG. 12*b* for constantly monitoring the integrity of the pipe in order to check for emerging cracks, corrosion etc. depending of the pipe's material and to provide early warning alerts for possible emerging leaks. In order to retain the gantry 82 in position around the pipe, end caps 85 may be provided on both sides of the gantry 82 as shown in FIG. 12*c* so as to form a generally cylindrical enclosure around the pipe that accommodates the γ-ray imaging assembly 81. The end caps 84 may also serve as a protective mechanical and environmental shielding of the γ-ray imaging assembly 81. It is seen in FIG. 12*d* that the system 80 covers only a small critical section of a long pipe, for example a joint area. However, the same principle may be used to image any length of coverage along a pipe regardless of diameter by increasing the length l of the cylindrical gantry 82.

It should be noted that the systems shown and described in FIGS. 11 and 12 are permanent fixtures that are constructed around the pipe, typically during installation. Since they employ a very low rate γ-source, can be battery powered and will operate for many years without the need to replace the battery and thus provide constant monitoring of the pipe or of a critical section thereof. This is distinct from known flow-meters that use γ-sources to monitor the density of liquid flowing inside of a pipe and which are fixed in space and do not move relative to the pipe.

It should also be noted that in a typical application employing a cylindrical gantry of the type shown in FIGS. 10 and 12, the object to be imaged is disposed inside a stationary gantry and the γ-source 11 and the detector 12 are adapted to move together around an inside periphery of the gantry. However, it is also possible to support the γ-source 11 and the detector 12 on a traveler that rides around the outside of the gantry so as to encircle an object to be imaged while still allowing lateral movement of the γ-source 11 and the detector 12. In either case, the gantry serves as an anchor for supporting the γ-source 11 and the detector 12 and for facilitating 3-D motion thereof around the object.

The invention claimed is:

1. A γ-ray scanner comprising a Solid-State Single-Photon Detector ("SSSPD") and a γ-ray source that is a radioisotope having an α-activity of about 35 kBq or less;
   said γ-ray scanner being configured for permanent installation in spatial relationship to a fixed object for inspecting the object over a prolonged period of time, said γ-ray scanner comprising a unitary imaging assembly that includes:
   a stationary hollow cylindrical gantry configured to accommodate the object;
   an armature that fixedly supports the γ-ray source and the SSSPD in mutual opposed alignment, so that they are constrained to move together;
   said armature being configured to ride around the gantry and to move laterally relative thereto in a direction parallel to a rotation axis of the armature so as to move the γ-ray beam around the object disposed inside the gantry and back and forth parallel to said rotation axis.

2. The γ-ray scanner according to claim 1, wherein the radioisotope is Americium oxide (Am-241).

3. The γ-ray scanner of claim 2, wherein the γ-ray source comprises less than 0.5 mg of material.

4. The γ-ray scanner according to claim 1, wherein the detector comprises a sensor formed of a single monolithic crystal of Cadmium-Zinc-Telluride (CZT) or Cadmium-Telluride (CdTe), and sub-divided (pixelated) in a 2D matrix of pixels.

5. The γ-ray scanner according to claim 4, wherein each pixel is attached to a respective active readout circuit, which is separate to the crystal but is coupled thereto by a respective connecting signal line.

6. The γ-ray scanner according to claim 5, wherein the pixels are divided into groups and the respective active readout circuits of each group of pixels are implemented by a respective ASIC.

7. The γ-ray scanner according to claim 1, wherein the γ-source and the detector are fixed in mutual opposed alignment via an integrated imaging assembly configured for movement in mutually orthogonal directions along a plane so as acquire stepwise γ-ray image fragments of an object disposed in said plane.

8. The γ-ray scanner according to claim 7, wherein the integrated imaging assembly comprises a first arm and a second arm connected to a moving element of an x-y table configured to move in predetermined sized steps in mutually orthogonal x and y directions whereby for each step, a γ-ray image fragment is acquired of a size that is determined by a cross-section of the γ-beam where it intersects the object.

9. The γ-ray scanner according to claim 1, including a traveller that is configured to ride around the gantry, the armature being configured to move along the traveller parallel to the rotation axis of the armature.

10. The γ-ray scanner according to claim 1, wherein the armature is arcuate in shape and is dimensioned to fit within an inside periphery of the gantry.

11. A system configured for permanent installation in spatial relationship to a pipe for monitoring a section of the pipe over a long time, said system comprising:
    a unitary imaging assembly that includes:
    a stationary hollow cylindrical gantry configured to surround said section of the pipe;
    a γ-ray scanner comprising a Solid-State Single-Photon Detector ("SSSPD") and a γ-ray source that is a radioisotope having an α-activity of about 35 kBq or less;
    an armature that fixedly supports the γ-ray source and the SSSPD in mutual opposed alignment, so that they are constrained to move together;
    said armature being configured to ride around an inside periphery of the gantry and the armature or the gantry being configured to move laterally in a direction parallel to a rotation axis of the armature so as to move the γ-ray beam and the SSSPD around and along the pipe at a sufficiently slow rate that completely exposes the section of pipe to the γ-ray source and thus produces a complete image of said section.

12. The system according to claim 11, wherein the gantry is configured to ride along a fixed rail disposed proximate the pipe.

13. The system according to claim 11, wherein the γ-source is attached to the gantry via an extension tube in order to emit a conical beam that images a larger area of the pipe during each imaging step.

14. The system according to claim 11, wherein the radioisotope is Americium oxide (Am-241).

15. The γ-ray scanner of claim 14, wherein the γ-ray source comprises less than 0.5 mg of material.

16. A 3-dimensional γ-ray scanner comprising:
    an imaging assembly including at least one Solid-State Single-Photon Detector ("SSSPD") and a respective γ-ray source that is a radioisotope having an α-activity of about 35 kBq or less;
    said imaging assembly being configured for relative rotation and translation with respect to an object disposed therein so as to produce successive images that allow construction of a 3-dimensional image of the object.

17. The system according to claim 16, wherein the radioisotope is Americium oxide (Am-241).

18. The γ-ray scanner of claim 16, wherein the γ-ray source comprises less than 0.5 mg of material.

* * * * *